US009161951B2

(12) United States Patent
Gupta

(10) Patent No.: US 9,161,951 B2
(45) Date of Patent: Oct. 20, 2015

(54) PARENTERAL NUTRITION COMPOSITION CONTAINING IRON

(76) Inventor: Ajay Gupta, Cerritos, CA (US)

( * ) Notice: Subject to any disclaimer, the term of this patent is extended or adjusted under 35 U.S.C. 154(b) by 1328 days.

(21) Appl. No.: 11/644,527

(22) Filed: Dec. 22, 2006

(65) Prior Publication Data
US 2007/0148259 A1 Jun. 28, 2007

Related U.S. Application Data

(60) Provisional application No. 60/753,815, filed on Dec. 23, 2005.

(51) Int. Cl.
| A61K 9/107 | (2006.01) |
| A61K 31/195 | (2006.01) |
| A61K 33/26 | (2006.01) |
| A61K 33/42 | (2006.01) |
| A61K 31/70 | (2006.01) |
| A23L 1/29 | (2006.01) |
| A23L 1/30 | (2006.01) |
| A23L 1/304 | (2006.01) |
| A23L 1/305 | (2006.01) |
| A61K 9/00 | (2006.01) |
| A61K 45/06 | (2006.01) |

(52) U.S. Cl.
CPC .............. *A61K 33/42* (2013.01); *A23L 1/293* (2013.01); *A23L 1/30* (2013.01); *A23L 1/304* (2013.01); *A23L 1/3006* (2013.01); *A23L 1/3051* (2013.01); *A61K 9/0029* (2013.01); *A61K 31/195* (2013.01); *A61K 31/70* (2013.01); *A61K 33/26* (2013.01); *A61K 45/06* (2013.01); *A23V 2002/00* (2013.01)

(58) Field of Classification Search
None
See application file for complete search history.

(56) References Cited

U.S. PATENT DOCUMENTS

| 3,530,216 | A | 9/1970 | Cavalli et al. ................. 424/128 |
| 4,315,942 | A | 2/1982 | Corden ......................... 424/265 |
| 4,329,332 | A | 5/1982 | Couvreur et al. .................. 424/9 |
| 4,753,963 | A | 6/1988 | Jandacek et al. .............. 514/552 |
| 4,867,963 | A | 9/1989 | Maurer et al. ..................... 424/9 |
| 5,447,732 | A | 9/1995 | Tanimoto et al. ............... 426/74 |
| 6,537,976 | B1 | 3/2003 | Gupta ............................. 514/52 |
| 6,541,029 | B1 * | 4/2003 | Namba et al. ................. 424/450 |
| 6,572,884 | B1 | 6/2003 | Pai et al. ....................... 424/455 |
| 6,689,275 | B1 | 2/2004 | Gupta ........................... 210/647 |
| 6,779,468 | B1 | 8/2004 | Gupta |
| 6,960,571 | B2 * | 11/2005 | Helenek et al. ................. 514/53 |

FOREIGN PATENT DOCUMENTS

WO WO 01/00204 A1 1/2001 ...................... 31/295

OTHER PUBLICATIONS

Reprint of Lavoie et al., Journal of Pediatric Gastroenterology & Nutrition(1997), vol. 25, No. 3, pp. 307-311, Reprint pp. 1-10.*
Bistrain et al., "Stability of lipid injectable emulsion-based parenteral nutrition admixtures with a novel parenteral iron doage form", *American Association of Pharmaceutical Scientists*, 2006 Annual Meeting and Exposition, Nov. 1, 2006.
Porter et al., "Safety of Iron Dextran in Total Parenteral Nutrition: A Case Report", *Journal of the American College of Nutrition*, 7(2): 107-110, 1998.
Sayers et al., "Supplementation of Total Parenteral Nutrition Solutions with Ferrous Citrate", *Journal of Parenteral and Enteral Nutrition*, 7(2): 117-120, 1983.
Geisser et al., "Fat, carbohydrate, minerals, and vitamins in parenteral nutrition", *Internal Medicine*, 4: 76-82, 1988.
Norton et al., "Iron Supplementation of Total Parenteral Nutrition: A Prospective Study", *Journal of Parenteral and Enteral Nutrition*, 7(5): 457-461, 1983.
Kumpf et al., "Parenteral Iron Dextran Therapy", *DICP, The Annals of Pharmacotherapy*, 24: 162-166, 1990.
Gupta et al., "Treatment of iron deficiency anemia: Are monomeric iron compounds suitable for parenteral administration", *J. Lab. Clin. Med.*, 371-378, 2000.
Gupta et al., "Dialysate iron therapy: Infusion of soluble ferric pyrophosphate via the dialysate during hemodialysis", *Kidney International*, 55: 1891-1898, 1999.
Maurer et al., "Preliminary Studies on Magnetic Resonance Contract Enhancement of Acute Myocardial Infarction", *Investigative Radiology*, 25: 153-163, 1990.
Ovid Medline® Abstract 3129481, abstracting Porter et al., "Safety of iron dextran in total parenteral nutrition: a case report", *J. Am. College of Nutrition*, Apr. 1988; 7(2): 107-10.
Ovid Medline® Abstract 8263659, abstracting Harraki et al., "Influence of copper, iron, and zinc on the physicochemical properties of parenteral admixture", *J. Parent. Sci. & Technol.*, Sep. 1993; 47(5): 199-204.
Ovid Medline® Abstract 8875535, abstracting Burns et al., "Effect of iron-supplemented total parenteral nutrition in patients with iron deficiency anemia", *Nutrition*, Jun. 1996; 12(6): 411-5.
Ovid Medline® Abstract 9285382, abstracting Lavoie et al., "Bound iron admixture prevents the spontaneous generation of peroxides in total parenteral nutrition solutions", *J. Ped. Gastro. & Nutri.*, Sep. 1997; 25(3): 307-11.
Khaodhiar et al., "Iron Deficiency in Patients Receiving Home Total Parenteral Nutrition", *Journal of Parenteral and Enteral Nutrition*, 26(2): 114-119, 2002.
Extended European Search Report, for PCT/US2006/048772, Appln. No. 06847907.0, Applicant Gupta, Ajay, Issued Jan. 27, 2012.
Ajay Gupta and Alvin L. Crumbliss, "Treatment of iron deficiency anemia: Are monomeric iron compounds suitable for parenteral administration?" Div. of Nephrology, Henry Ford Hospital, Detroit and Chemistry Dept., Duke University, Durham (2000).
C. Washington, "The stability of intravenous fat emulsions in total parenteral nutrition mixtures," Elsevier Science Publ. B.V., Biomedical Div. (1990).
Office Action issued Feb. 23, 2011, in Chinese Patent Application No. 200680052611.4.
Purported English language translation of the Office Action in Chinese Patent Application No. 200680052611.4, (2011).

* cited by examiner

Primary Examiner — Abigail Fisher
Assistant Examiner — Frank Choi
(74) Attorney, Agent, or Firm — Marshall, Gerstein & Borun LLP

(57) ABSTRACT

Bioavailable iron-containing parenteral nutrition compositions are provided that are physico-chemically stable. Iron is present in the form of soluble ferric pyrophosphate. Methods of preparation and use of the compositions are provide, as well as kits.

27 Claims, No Drawings

PARENTERAL NUTRITION COMPOSITION CONTAINING IRON

CROSS-REFERENCE TO RELATED APPLICATION

This application claims the benefit under 35 U.S.C. 119(e) of U.S. Provisional Patent Application 60/753,815, filed Dec. 23, 2005, the entire disclosure of which is incorporated herein by reference.

FIELD OF THE INVENTION

The invention relates to a composition containing bioavailable iron suitable for parenteral nutrition.

BACKGROUND OF THE INVENTION

Parenteral nutrition (PN), also known as parenteral hyperalimentation, is a medical treatment that supplies nutrition-maintaining compositions intravenously, and is indicated for a variety of mammalian disorders, such as cancer, gastrointestinal diseases, major body burns, extensive wounds, and AIDS. Partial parenteral nutrition supplies only part of daily nutritional requirements, supplementing oral intake. Many hospitalized patients receive dextrose or amino acid solutions by this method. Total parenteral nutrition treatment (TPN) supplies all daily nutritional requirements intravenously, circumventing the gut. TPN may be employed following surgery, when feeding by mouth or using the gut is not possible, when a patient's digestive system cannot absorb nutrients due to chronic disease, or, if nutrition cannot be met by enteral feeding and supplementation. Premature and sick infants often require extended periods of TPN.

Compositions for parenteral nutrition generally contain at least water, glucose, amino acids, and optionally emulsified fats. They may be aseptically compounded from amino acid solutions, dextrose solutions, and/or lipid emulsions. PN compositions may further contain vitamins, electrolytes and essential trace elements.

PN compositions generally contain only negligible amounts of iron. Because of concerns about incompatibility and toxicity, iron is not routinely added to PN admixtures.

Patients who require TPN may develop iron deficient anemia despite administration of hematopoietic nutrients (e.g., folate, vitamin $B_{12}$, pyridoxine, ascorbic acid, copper, zinc, and amino acids). Iron deficiency is a primary cause of anemia in patients receiving TPN and reflects a patient's inability to compensate for blood losses associated with underlying disease, multiple surgeries, or frequent phlebotomies.

Iron deficiency is corrected by the administration of iron-containing compounds. In general, healthy subjects who suffer from iron deficiency ingest oral preparations containing iron salts as a safe, cheap and effective means of replenishing iron stores. Patients, however, are frequently non-compliant with oral iron supplements due to associated gastrointestinal side-effects, e.g., nausea, vomiting, bloating, discomfort, indigestion, heartburn, and constipation. In patients receiving TPN, administration of oral iron may not be feasible either because the mechanical factors that preclude use of enteral nutrition also preclude the use of oral and/or enteral iron, or patients may not be able to absorb oral iron, such as patients with malabsorption syndrome. Furthermore, oral iron administration is commonly associated with unpleasant and/or deleterious gastrointestinal side effects thereby resulting in poor compliance.

Various forms of iron have been suggested for intravenous administration, including, by way of example, low molecular weight ferrous iron compounds, such as ferrous citrate or ferrous gluconate, and iron bound to polymeric materials, such as iron dextran and iron saccharates. Formulations containing simple iron salts, such as iron chloride, sulfate or ascorbate, are considered too toxic for parenteral administration, since transfer of these iron salts to the patient's blood liberates free iron, i.e., iron that is not bound to a natural or synthetic ligand, such as transferrin, or ferritin. Free iron, whether in its +2 (ferrous) or +3 (ferric) oxidation state, is a transition element capable of catalyzing free radical generation and lipid peroxidation. The ferrous (Fe(II)) ion is reactive, and by a series of cyclic redox reactions, leads to the production of highly reactive hydroxyl radicals by the Fenton reaction, or alkoxyl and peroxyl radicals from the breakdown of lipid peroxides. Likewise, the highly charged ferric (Fe(III)) aquo ion will tend to precipitate at physiological pH due to hydrolysis reactions to form insoluble hydroxides, and its interactions with plasma proteins may result in their denaturation and partial precipitation. All of these actions are toxicities with serious adverse effects and have prevented clinical use of conventional ferrous or ferric iron salts in formulations that are administered intravenously.

Colloidal iron compounds that are iron-carbohydrate complexes are currently formulated for parenteral administration of iron. In the United States, colloidal iron compounds approved by the U.S. Food and Drug Administration for i.v. administration include iron dextran (INFeD®, Watson Pharma, Inc.; Dexferrum®, American Regent, Inc.), iron gluconate (Ferrlecit®, Watson Pharma, Inc.), or iron sucrose (Venofer®, American Regent, Inc.). Intravenous administration of colloidal iron compounds such as these is known to cause serious adverse effects, including pain, severe and/or life-threatening anaphylactoid reactions, organ toxicity, release of catalytically active iron that is associated with higher risk of or exacerbation of infection and possibly cancer, and oxidative stress and chronic inflammation that is causatively associated with atherosclerosis, coronary artery disease, and strokes (*Physicians' Desk Reference*, 58$^{th}$ Ed., pages 568-570, 3319-3322 (2004)). Furthermore, parenteral formulations containing conventional colloidal iron preparations have potent, but highly variable, cytotoxic potentials (Zager et al., 2004, *Kidney Intl.* 66: 144-156). Zager et al. concluded that parenteral formulations of colloidal iron complexes have potent cytotoxic potentials that can be exhibited at clinically relevant iron concentrations. The persistence of polymeric iron complexes in the circulation for several days following i.v. infusion may allow uptake by microorganisms and thereby promote microbial growth. Recent studies have also shown that i.v. administration of colloidal iron compounds may be associated with an increased morbidity and mortality from infections (Collins et al., 1998, *J. Am. Soc. Nephrol.* 9: 205A). Therefore, the use of i.v. colloidal iron requires close monitoring for adverse patient responses with each administration.

It has been proposed that maintenance parenteral nutrition patients receive intravenous polymeric iron supplements. A prospective study to evaluate the intravenous iron dextran (Imferon®, Merrill National Laboratories, Cincinnati, Ohio, US) dosage needed to restore serum iron levels in patients receiving TPN showed that 87.5-175 mg/week iron effectively raised serum iron levels over a 3 week period (Norton et al, 1983, *Journal of Parenteral and Enteral Nutrition* 7:457-461). For ease of administration polymeric iron dextran has been administered as an additive to parenteral nutrition mixtures (Porter et al, 1988, *Journal of American College of Nutrition* 7(2): 107-110).

The compatibility of iron with parenteral nutrition admixtures, however, has not been clearly established. One study has shown 1-day compatibility of ferrous citrate, a monomeric ferrous salt, with a single parenteral nutrition component, amino acid solution (Sayers et al., 1983, *J. Parenter. Enteral Nutr.* 7(2): 117-120). A second study has shown compatibility of iron dextran with amino acid-dextrose parenteral admixtures (Wan et. al., 1980, *Am. J. Hosp. Pharm.* 37: 206-210.) In contrast, several studies found that iron dextran added to TPN formulation caused breakdown of the admixture, coalescence of lipid droplets, and cracking and creaming of the lipid component (Driscoll et al., 1995, *Am. J. Health-Syst. Pharm.* 52:623-634; Vaughan et al., 1990, *Am. J. Hosp. Pharm.* 47:1745-1748). The effect of colloidal iron dextran on the stability of parenteral nutritional (PN) emulsions has been analyzed (Driscoll et al., 1995, supra). Driscoll et al. (1995, supra) determined that the trivalent cation content derived from colloidal iron dextran was the only variable that affected the stability of nutritional emulsions, accounting for approximately 60% of a potentially dangerous increase in fat particle sizes observed. In addition, a percentage of large fat particles (i.e., fat particles greater than 5 μm in diameter; PFAT5) that was greater than 0.4% was observed to be associated with unstable PN emulsions and disruption of their integrity.

Product labeling for each of the conventional colloidal iron-containing formulations warns specifically that the formulation is not to be added to parenteral nutrition solutions for intravenous administration (*Physicians' Desk Reference*, 58$^{th}$ Ed., pages 568-570, 3319-3322 (2004)). There is also concern that prolonged iron administration in parenteral nutrition may have undesirable adverse effects. Iron overload has been reported in children receiving prolonged iron supplementation in TPN (Ben Hariz et al., 1993, *J Pediatr.* 123: 238-241)

Consequently, there is a need for an alternative and more physiologic method of administering bioavailable iron intravenously as a component of a parenteral nutrition composition. The present invention addresses that need.

SUMMARY OF THE INVENTION

The invention provides a composition comprising bioavailable iron suitable for parenteral nutrition. In one embodiment, the composition comprises a therapeutically effective amount of soluble ferric pyrophosphate: amino acids; carbohydrate; and a pharmaceutically acceptable carrier. In another embodiment, the composition further comprises lipid. The composition is characterized by physico-chemically stability. In one embodiment, the composition is physico-chemically stable for at least about 24 hours following preparation, when the composition is maintained at a temperature of about 25° C.

In one embodiment of the invention, the mean droplet size of the composition is less than about 500 nanometers for at least about 30 hours following preparation, when the composition is maintained at a temperature of about 25° C. In another embodiment, the mean droplet size of the composition is less than about 285 nanometers for at least about 30 hours following preparation, when the composition is maintained at a temperature of about 25° C.

In another embodiment, the globule size distribution of the composition, expressed as the volume-weighted percent of fat greater than 5 μm in the composition, is less than about 0.05% at about 30 hours following preparation, when the composition is maintained at a temperature of about 25° C. In yet another embodiment, the globule size distribution of the composition, expressed as the volume-weighted percent of fat greater than 5 μm in the composition, is less than about 0.03% at about 30 hours following preparation, when the composition is maintained at about 25° C.

In one embodiment of the invention, the soluble ferric pyrophosphate is added to the composition such that the iron content present in the composition in the range of about 1 mg/L to about 150 mg/L.

In certain embodiments of the composition of the invention, amino acids are present in the range from about 2.5% to about 7% (w/v), and carbohydrate is present in the range from about 5% to about 20% (w/v). In some embodiments of the invention, the carbohydrate comprises dextrose. In certain embodiments of the invention where the composition comprises lipid, the lipid is present in the range from about 2% to about 5% (w/v).

A method for preparing a composition suitable for parenteral nutrition is provided, comprising aseptically combining soluble ferric pyrophosphate, amino acids, carbohydrate and a pharmaceutically acceptable carrier, and optionally, lipid.

A method for providing parenteral nutrition comprising bioavailable iron is also provided, by administering to an individual, a composition according to the present invention.

A further method for providing parenteral nutrition comprising bioavailable iron to an individual is provided. The method comprises intravenously administering a first composition comprising amino acids, carbohydrates and a pharmaceutically acceptable carrier, and intravenously administering a second composition comprising lipid. At least one of the first and second compositions contains soluble FePPi.

A kit is provided for providing parenteral nutrition comprising a first container containing a first composition comprising amino acids, carbohydrates and a pharmaceutically acceptable carrier, a second container containing a second composition comprising lipid. At least one of the first and second compositions contains soluble FePPi, or said soluble FePPi is contained in the kit in a third container

DETAILED DESCRIPTION OF THE INVENTION

Definitions

As used herein, the singular forms "a", "an" and "the" include the plural, unless the context clearly dictates otherwise.

The term "individual" (as in the subject of a treatment) means both mammals and non-mammals. Mammals include, for instance, humans, non-human primates, cattle, horses, sheep, pigs and goats.

As used herein, "bioavailable iron" refers to iron in a chemical and physical form that allows it to be absorbed and used by the body of an organism.

As used herein, an "instructional material" includes a publication, a recording, a diagram, or any other medium of expression which can be used to communicate the usefulness of the kit for its designated use in practicing a method of the invention. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The terms "sterile" and "sterilized" as used herein have their conventional meanings as understood by skilled artisans when referring to the sterility required pharmaceutically for intravenous preparations. Sterilization is achieved conventionally, either by application of heat (e.g., high-pressure steam sterilization or high-temperature short time steam sterilization) or through the use of filters having a pore-size sufficiently small to exclude pathogens.

The term "suitable for intravenous injection" as used herein has its conventional meaning as understood by skilled artisans when referring to a composition that meets the general requirements for solutions for injection as presented in the General Chapter of the U.S. Pharmacopoeia entitled "Injections." (U.S. Pharmacopoeia, U.S. Pharmacopeias Convention, Inc., Rockville, Md., 2004.)

The terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions, or (d) returning a clinical value to the concentration range normally found in a subject.

The phrase "therapeutically effective" is intended to qualify the amount of soluble ferric pyrophosphate for use in the intravenously administered therapy which will achieve the goal of providing a biologically available (i.e., bioavailable) concentration of ferric iron to effect abating, mitigating, reducing or preventing, for example, an iron deficiency disorder, while avoiding adverse side effects typically associated with conventional low molecular weight iron salts or polymeric iron-saccharate preparations.

By the term "parenteral nutrition composition" is meant a hyperalimentation composition for intravenous administration comprising one or more components selected from the group consisting of a carbohydrate solution, an amino acids solution, and lipid.

By the term "physico-chemically compatible" with respect to a component of a parenteral nutrition composition is meant that a disruption of the composition is not observed, as determined by the observation of phase separation, creaming, particulate formation, an increase in the percentage of lipid globules having a diameter greater than 5 μm as measured by conventional light scattering, light obscuration, or particle-sizing techniques, or the like.

It is understood that any and all whole or partial integers between any ranges set forth herein are included herein.

Parenteral Nutrition Composition

The inventor has discovered, unexpectedly and uniquely, that parenteral nutrition compositions and soluble ferric pyrophosphate are physico-chemically compatible. Specifically, the soluble ferric pyrophosphate-containing compositions of the present invention are physico-chemically stable and do not undergo degradation, increases in the size of fat globules, creaming, or phase, separation over at least about 30 hours at room temperature (about 25° C.). In contrast, conventional polymeric iron complexes, when aseptically compounded with PN admixtures containing lipid, cause degradation and breakdown of the resulting PN admixture, increases in the size of fat globules, creaming, or phase-separation within a few hours (Driscoll et al., 1995, supra).

Accordingly, the invention provides an iron-containing composition that is useful for parenteral nutrition and for total parenteral nutrition therapies. In one embodiment, the composition comprises soluble ferric pyrophosphate, amino acids, and carbohydrate. In one embodiment, the composition further comprises lipid. In a preferred embodiment, the carbohydrate is dextrose. The components of the composition are present in nutritionally effective amounts, as hereinafter exemplified.

Low-dose iron parenteral nutrition therapy, as provided by administering the soluble ferric pyrophosphate-containing parenteral nutrition admixture of the present invention, affords numerous benefits to the recipient. The soluble ferric pyrophosphate-containing parenteral nutrition admixture provides a slow, continuing transfer of biocompatible iron to the patient during infusion. The amount of iron in the admixture can be readily and repeatedly adjusted according to the patient's need. Once a steady state is reached, patients are likely to need less intensive monitoring of iron stores than patients receiving oral or conventional i.v. colloidal iron therapy.

Following their intravenous administration, prior art conventional colloidal iron compounds (e.g., iron dextran, iron sucrose and iron gluconate ($M_r$ 45-350 kDa)) must be processed in the reticuloendothelial system of the recipient before iron is delivered to transferrin. In general, only about 50-85% of the iron delivered intravenously as a colloidal iron complex is bioavailable and utilized for hemoglobin generation (Gupta et al., 2000, J. Lab. Clin. Med. 136: 371-378). In contrast, the soluble ferric pyrophosphate-containing compositions of the present invention are cleared from the circulation more rapidly, since ferric pyrophosphate binds directly to transferrin. When soluble ferric pyrophosphate is administered to patients via a parenteral nutrition admixture in accordance with the present invention, slow administration of iron is facilitated, and iron status is easier to monitor. Moreover, parenteral nutrition compositions of the invention are easily administered to patients at home. In patients receiving TPN, administration of oral iron may not be feasible either because the mechanical factors that preclude use of enteral nutrition also preclude the use of oral and/or enteral iron, or patients may not be able to absorb oral iron, such as patients with malabsorption syndrome. Furthermore, oral iron administration is commonly associated with unpleasant and/or deleterious gastrointestinal side effects thereby resulting in poor compliance. By eliminating or reducing the need for oral iron supplementation and thereby the pill burden, the parenteral nutrition composition of the present invention will likely improve quality of life and increase compliance with other medications.

The composition of the invention in one embodiment is an admixture of soluble ferric pyrophosphate and a conventional parenteral nutrition preparation. Conventional parenteral nutrition preparations may contain a variety of nutritional components, which are varied based on the particular needs of the recipient individual. As is known by the skilled artisan, patient-specific factors should be considered when selecting an appropriate parenteral formulation. Patient variables include but are not limited to: nutritional status and requirements, electrolyte balance, digestive and absorptive capacity, disease state, renal function, and medical or drug therapy. One of skill in the art is familiar with determining the appropriate parenteral formulation for a person in need of parenteral nutrition and doing so is routine in the art.

Conventional parenteral nutrition preparations useful in preparing the iron-containing compositions of the invention generally provide the following quantities of components on a daily basis: water at about 30 to about 40 milliliter per kilogram body weight (ml/kg); energy at about 20 to about 60 kilocalorie per kilogram body weight (kcal/kg), depending on energy expenditure of the patient; and amino acids at about 0.8 to about 3.0 gram per kilogram body weight (g/kg), depending on the degree of catabolism of the patient. Energy is provided primarily by carbohydrate, and when present, lipid components of the parenteral nutrition composition. Optional components include vitamins, minerals and electrolytes.

Accordingly, clinically useful parenteral nutrition preparations useful in preparing the composition of the invention may be aseptically compounded to contain amino acids (range, 2.5-7% (w/v)) and carbohydrate, such as hydrated glucose or dextrose, (range, 5-20% (w/v)). Lipid is optionally and preferably present in the form of an emulsion (range, 2-5% (w/v)). Additives, such as trace-element solutions and multi-vitamin solutions not containing iron, are optionally included. The composition of the invention further comprises soluble ferric pyrophosphate in a therapeutically effective amount.

About 15-20% of patients with acute pancreatitis develop hypertriglyceridemia. Some of these patients with fulminant or protracted acute pancreatitis cannot be fed orally for prolonged periods and require parenteral nutrition. Administration of lipids, as a component of parenteral nutrition mixture, would be contraindicated in such patients. For patients in whom lipid administration is contraindicated, parenteral nutrition preparations useful in preparing a composition of the present invention are aseptically compounded to contain amino acids (range, 2.5-7% (w/v) and carbohydrate, such as hydrated glucose or dextrose, (range, 5-20% (w/v)); but are lacking in lipid. Additives, such as trace-element solutions and multi-vitamin solutions not containing iron, are optionally included. The composition of the invention further comprises soluble ferric pyrophosphate in a therapeutically effective amount.

Soluble Ferric Pyrophosphate

Ferric pyrophosphate is a monomeric iron compound that is available in two different forms. Pure ferric pyrophosphate ("FePyP") is a tan powder having the molecular formula $Fe_4(P_2O_7)_3$, a molecular weight (MW) of 745.2, and CAS Reg. No. 10058-44-3. FePyP is insoluble in water. The second form, soluble ferric pyrophosphate ("soluble FePPi") is a green to yellow-green powder, has a molecular composition of $(Citrate)_4.2Fe.(P_2O_7).xNa$, CAS Reg. No. 1332-96-3, and an approximate molecular weight of about 1000-1500. Soluble FePPi is a chelate in which ferric iron is chelated to pyrophosphate and citrate; the chelate is rendered water-soluble by the presence of citrate. The solubility of soluble FePPi in water is greater than 1000 mg/ml, and thus exceeds the solubility needed for low-dose iron-repletion via parenteral nutrition administration. Thus, soluble FePPi differs from FePyP in its composition, color, molecular weight, and solubility in water.

Soluble FePPi occurs as thin, apple green, transparent scales, or pearls or granules or powder. Soluble FePPi can be prepared a number of ways known in the art, including treating ferric citrate with sodium pyrophosphate in solution (*Ferri Pyrophosphas Solubilis*, in United States Pharmacopeia, vol. 8, New York, 1907, p. 161) or by chemically reacting FePyP with citric acid and sodium hydroxide. Soluble FePPi is available commercially as a food grade chemical (Dr. Paul Lohmann Chemische Fabrik GmbH, Emmerthal, Germany).

Soluble FePPi has a variable molecular weight and contains a variable amount of iron, ranging from 10.5 to 12.5% (w/w). Because of the variability in the percentage of iron content it is routine practice in the art to refer to the content of elemental iron rather than the corresponding amount of the iron chelate or complex since it is the amount of iron that is clinically relevant. Therefore, in this application, unless stated otherwise, the amount of soluble ferric pyrophosphate refers to the amount of elemental iron provided by the chelate, and not the amount of the chelate itself. The concentration of soluble FePPi in the parenteral nutrition composition of the invention will depend on the recipient's needs. The calculation of iron need is well known to those skilled in the art. Generally, the concentration of elemental iron (as soluble ferric pyrophosphate) in the parenteral nutrition composition of the invention is preferably in the range of about 1 to about 150 mg/L (corresponding to about 0.0001% to about 0.015% (w/v)), and preferably from about 1 to about 50 mg/L, or as needed by the recipient. The skilled artisan is familiar with assessing iron deficiency and determining the quantity necessary to replete iron stores in iron deficient patients and maintain iron stores in those with ongoing iron losses that cannot be met by diet or nutritional formulations (Norton et al., 1983, *Journal of Parenteral and Enteral Nutrition* 7:457-461). In the most preferred embodiment only about 5-25 mg iron is infused per day. The iron may be administered daily with the parenteral nutrition admixture when a patient is iron deficient. On the other hand, when the objective is to maintain the patient in an iron-replete state, iron may be added to the PN on alternate days or as infrequently as once a week or even once every 2 weeks. Conventional methods of assessing iron status include measuring ferritin, total iron binding capacity, transferrin saturation, hemoglobin and red blood cell indices. As with any component of the composition of the invention, periodic reevaluation of the patient's need for iron supplementation is preferable.

Lipid

Lipid in the parenteral nutrition composition of the invention, when present, is generally provided in the form of a lipid emulsion that comprises animal and/or vegetable oil and an emulsifier agent. The oil advantageously comprises a source of essential fatty acids (linoleic acid and linolenic acid).

Oils useful for the preparation of a lipid emulsion suitable as the lipid component in the parenteral nutrition composition of the invention include, but are not limited to, cotton seed oil, sesame oil, peanut oil, olive oil, safflower oil, soybean oil, fish oil and medium-chain triglycerides. Methods of extracting and refining animal or vegetable oils are well known in the art. For example, International Patent Application No. PCT/CA00/00028 describes a method of refining animal or vegetable oils using low heat. The use of low temperature methods minimizes the amount of detrimental oxidized and trans-fatty acids that are present in the purified oil. Other methods are available in the art and well known to one of skill in the art.

Emulsifying agents useful for preparing a lipid emulsion suitable as the lipid component in the parenteral nutrition composition of the invention are preferably phospholipids of natural, synthetic or semi-synthetic origin. Examples of such phospholipids include, but are not limited to, egg phosphatidylcholine, egg lecithin, soy lecithin, L-α-dipalmitoyl phosphatidylcholine (DPPC), DL-α-dipalmitoyl phosphatidylethanolamine (DPPE), and dioleoyl phosphatidylcholine (DOPC).

Methods of preparing lipid emulsions using purified oil are also well known in the art. See for instance U.S. Patent Publication No. 20060127491. In general, the core lipid is first mixed with an emulsifier and, optionally, an antioxidant. The emulsion is then prepared by slowly adding this oil phase into water with constant agitation. If an osmolality modifier is being used, it is added to the water prior to mixture with the oil phase. The pH can be adjusted at this stage, if necessary, and the final volume adjusted with water, if required.

Commercially-available lipid emulsions useful in preparing the parenteral nutrition composition of the invention include, but are not limited to, INTRALIPID and STRUCTOLIPID (Fresenius, Germany), LIPOSYN, LIPOSYN II and LIPOSYN III (Hospira Inc.), TRAVAMULSION (Baxter), SOYACAL (Alpha Therapeutics) and LIPOFUNDIN (B. Braun Medical Inc.). These lipid emulsions are composed of a vegetable oil, such as soybean oil or safflower oil, an emulsifying agent, such as egg phospholipids, glycerol, and water. OMEGAVEN (Fresenius, Germany) is a 10% fish oil emulsion with a high percentage of omega-3 fatty acids, eicosapentaenoic acid (EPA) and docosapentaenoic acid (DHA). Commercially available lipid emulsions are typically provided in 10%, 20% and 30% (w/v) concentrations. A 10% lipid emulsion has about 1.1 kcal per milliliter (kcal/ml). A 20% lipid emulsion has about 2.0 kcal/ml and a 30% lipid emulsion has about 2.9 kcal/ml.

Current national guidelines recommend limiting fat intake to less than 30% of total daily kcals. Parenteral nutrition compositions of the invention preferably comprise between about 2% to about 5% (w/v) lipid. This range corresponds to about 0.2 kcal/ml to about 0.55 kcal/ml, which is generally sufficient to satisfy the daily requirement for lipid-derived kcals of a patient.

Carbohydrate

Carbohydrates are the most important source of energy in parenteral nutrition. Any carbohydrate (CHO) that is metabolized and utilized as a calorie source in vivo may be used in the composition of the invention. The carbohydrate may be simple monosaccharides, disaccharides, oligosaccharides, or complex carbohydrates. Carbohydrate sources which may be utilized in the formulation of the invention include hydrolyzed or nonhydrolyzed starches. Examples of carbohydrates useful in the composition of the invention include, but are not limited to, glucose, particularly D-glucose (dextrose); fructose; maltodextrin; corn syrup; corn starch; and xylitol. In one embodiment, the carbohydrate comprises D-glucose. In another embodiment, the carbohydrate comprises hydrated D-glucose.

The parenteral nutrition composition of the invention preferably comprises about 5% to about 20% (w/v) carbohydrate. This range is generally sufficient to provide the daily requirement for carbohydrate-derived kcals of a patient. Depending on the needs of the recipient, carbohydrate may provide, for example, between about 10% to about 80% of the total daily kcal, and preferably about 15% to about 60%. Dextrose for i.v. use provides 3.4 kcal/gram. Caloric values of other carbohydrates are known in the art or readily determined using conventional methods in the art. Commercially available sources of dextrose suitable for use in a parenteral nutrition compositions of the invention typically range from about 10% to about 70% (w/v) dextrose in sterile, nonpyrogenic, hypertonic, aqueous solution.

Amino Acids

L-Amino acids provide a biologically-available source of nitrogen. Preferably, the amino acid component of the parenteral nutrition composition of the invention comprises the amino acids, particularly the L-amino acids, that cannot be produced by the body. These nine essential amino acids are isoleucine, leucine, lysine, methionine, phenylalanine, threonine, tryptophan, histidine and valine. Non-essential amino acids may also be included, such as alanine, glycine, arginine, proline, tyrosine, glutamic acid, aspartic acid and serine. Glutamine is important in stress metabolism, such as may occur due to severe illness, and therefore is useful in parenteral nutrition compositions in some embodiments. The amino acids contained in the amino acid component may be in a free form or in a form of a salt. Thus, as used herein, "amino acid" includes the free form and the salt form. An example of the salt of an amino acid is a salt thereof with an organic acid such as malic acid, oleic acid, acetic acid, glutamic acid or hydrochloric acid.

The ratio of individual amino acids in the composition of the invention is not particularly limited and can be determined according to any known index in the art. Exemplary indices are disclosed, for instance, in U.S. Pat. No. 5,767,123.

Amino acids are present in the composition of the invention in a range, for example, of about 2.5% to about 7% (w/v). Commercially available amino acid solutions useful in the composition of the invention include AMINOSYN, AMINOSYN II and AMINOSYN specialty amino acid solutions (Hospira Inc.), FREAMINE II (B. Braun Medical), AMINVEN (Fresenius Kabi, Germany) and PRIMENE and SYNTHAMIN (Baxter Clintec).

Additional Components

The composition of the invention may further comprise optional components including, but not limited to, vitamins, electrolytes, trace minerals and medicaments, such as heparin, insulin and H2 antagonists.

Vitamins useful in a parenteral composition of the invention include both fat soluble vitamins and water soluble vitamins. Fat soluble vitamins include retinol (vitamin A), 25-hydroxycholecalciferol (vitamin D), alpha- and/or gamma-tocopherol (vitamin E), and phylloquinone (vitamin K). Water soluble vitamins include thiamin (vitamin B1), riboflavin (vitamin B2), pyridoxin (vitamin B6), niacin (vitamin B3), folic acid, cobalamin (vitamin B12), biotin, panthothenic acid (vitamin B5), and ascorbic acid (vitamin C). Vitamins may be provided in daily amounts consistent with FDA Recommended Allowances for intravenous vitamins, as shown in Table 1, or as needed.

TABLE 1

| Vitamin | FDA daily amount |
| --- | --- |
| Thiamin | 6 milligram (mg) |
| Riboflavin | 3.6 mg |
| Pyridoxine | 6 mg |
| Cobalamin | 5 microgram (mcg) |
| Niacin | 40 mg |
| Folic acid | 600 mcg |
| Pantothenic acid | 15 mg |
| Biotin | 60 mcg |
| Ascorbic acid | 200 mg |
| Vitamin A | 3300 International Units (IU) |
| Vitamin D | 200 IU |
| Vitamin E | 10 IU |
| Vitamin K | 150 mcg |

Electrolytes useful in a parenteral composition of the invention include, for example, calcium, chloride, magnesium, phosphate, potassium, acetate, gluconate and sodium. Guidelines for daily requirements for electrolytes are provided in Table 2. Acetate is provided as needed to maintain acid-base balance. Appropriate compounds to provide any particular electrolyte are well known in the art.

TABLE 2

| Electrolyte | Daily requirement |
| --- | --- |
| Sodium | 60-150 mEq |
| Potassium | 60-240 mEq |
| Chloride | 60-150 mEq |
| Magnesium | 8-24 mEq |
| Phosphate | 15-30 mEq (or about 7-10 mMol per 1000 kcal) |
| Calcium | 9-22 mEq |

In one embodiment, the composition comprises monovalent cations (e.g., sodium and potassium) in the range of about 0 to about 150 mEq/L and divalent cations (e.g., calcium and magnesium) in the range of about 4 to about 20 mEq/L.

Trace minerals useful in a parenteral composition of the invention include, for example, chromium, copper, manganese, selenium, iodine, molybdenum and zinc. Trace minerals are provided in daily amounts consistent with FDA Recommended Allowances or as needed. The recommended daily amount for intravenous trace mineral for the most common trace minerals added to parenteral compositions for an adult is shown in Table 3.

TABLE 3

| Trace mineral | Recommended adult daily amount |
| --- | --- |
| Chromium | 10-15 mcg |
| Copper | 0.3-0.5 mg |
| Manganese | 60-100 mcg |
| Selenium | 20-60 mcg |
| Zinc | 2.5-5.0 mg |

Other optional components which may be added to the composition of the invention include, but are not limited to, nucleotides, beta-carotene, carnitine, taurine, and medicaments, such as insulin, heparin and H2 antagonists (e.g., ranitidine hydrochloride).

Preparation of Parenteral Nutrition Composition

The preparation of the parenteral nutrition composition of the invention follows conventional methods for preparing aseptic compositions suitable for intravenous administration. In one embodiment, appropriate amounts of separate, sterile concentrated solutions of soluble FePPi, amino acids, carbohydrate, a pharmaceutically acceptable carrier, and optionally lipid, are aseptically admixed to prepare a parenteral nutrition composition with the desired quantity of each component. In another embodiment, soluble FePPi is aseptically added to an already-admixed conventional parenteral nutrition formulation. In one aspect of the pre-mixed embodiment, the admixed parenteral nutrition formulation comprises amino acids and carbohydrate, and is supplemented with both soluble FePPi and lipid to prepare a parenteral nutrition composition of the invention. In another aspect, the pre-mixed parenteral nutrition formulation comprises lipid, amino acids and carbohydrate, and is supplemented with soluble FePPi to prepare a soluble FePPi-containing composition of the invention. Optional components, such as vitamins, trace minerals other than iron and electrolytes, are also aseptically added.

As shown herein, the admixed soluble Fe-PPi-containing parenteral nutrition compositions of the invention are stable for at least about 30 hours at room temperature (about 25° C.). Thus, the compositions may be prepared several hours in advance of administration. For instance, if the composition is designed for a 24 hour infusion, the composition may be prepared about 6 hours prior to the start of the infusion. Alternatively, the composition is prepared immediately prior to use. For example, the soluble ferric pyrophosphate can be added to a parenteral nutrition composition comprising lipid, amino acids and carbohydrate in a pharmaceutically acceptable carrier immediately before administration, for instance, at the patient's bedside. Advantageously, a soluble FePPi-containing parenteral nutrition composition of the invention is stable and can be safely administered for the duration of a 24 hour infusion.

The compositions of this invention may be formulated into suitable dosage forms for any mode of intravenous administration using conventional considerations of pharmacy (Gennaro A R, Ed. Remington: The Science and Practice of Pharmacy. 20$^{th}$ Edition. Baltimore: Lippincott, Williams & Williams, 2000). Formulations used for parenteral administration may be solutions, preferably aqueous solutions, emulsions or implants.

The soluble FePPi may be added to the parenteral nutrition composition or a component thereof as a concentrated sterile aqueous solution. Preferably the soluble FePPi solution is nonpyrogenic. A sterile solution of soluble ferric pyrophosphate is prepared by adding soluble ferric pyrophosphate to a pharmaceutically acceptable carrier with agitation and sterilizing the resulting solution. The pharmaceutical carrier is preferably water, preferably sterilized and nonpyrogenic water. Other pharmaceutically acceptable carriers compatible with the iron composition may also be employed. Optionally, the water contains a buffer to maintain the pH value with the range from about 5 to about 8. Optionally, the pH of the resulting soluble FePPi solution is adjusted with an aqueous alkali metal hydroxide solution to any pH value within the range of from about 5.0 to about 8.0, and preferably about 7.0. The alkali metal hydroxide is, for example, sodium hydroxide or potassium hydroxide, preferably sodium hydroxide.

In some embodiments of the soluble FePPi solution, the pharmaceutical carrier is an aqueous solution containing water for injection and one or more pharmaceutical auxiliaries and excipients that are added for conventional pharmaceutical purposes, such as increasing the osmolality, acting as anti-oxidants, and the like. The concentration of elemental iron (as soluble ferric pyrophosphate) in the pharmaceutical carrier is generally in the range of about 0.1 to about 50 mg/ml. Optionally, during manufacture, the pharmaceutical carrier is sparged with an inert gas, such as nitrogen or argon, to reduce the concentration of oxygen in the pharmaceutical carrier and the resulting soluble FePPi solution. Optionally, the exposure of the resulting solution to light is limited during manufacture and storage. The resulting soluble FePPi solution is sterilized using conventional methods known to those skilled in the pharmaceutical art. Sterilized solutions are packaged and stored in containers such as ampoules, syringes, vials, infusion bottles, flexible containers, etc. These manufacturing conditions may be scaled by one of skill in the art using fully conventional considerations to prepare small and large volumes.

A multiple-chamber bag may be used to facilitate the aseptic compounding of soluble FePPi and other solutions to prepare the parenteral nutrition compositions of the invention. Such multiple-chamber containers are well known in the art and are advantageous in reducing the risk of contamination and mixing errors, while offering rapid and accurate preparation of admixtures. The bag chambers are separated, for instance, by septums, by separation rods, frangible valves or other openable seals. To admix the solutions, the seals are opened, and the contents of the chambers are mixed. For instance, a three-chamber bag containing a sterile solution of FePPi in one chamber, a sterile carbohydrate solution in a second chamber and a sterile amino acid solution in a third channel is contemplated. Sufficient room is provided to permit the optional addition of lipids. Also contemplated is a three-chamber bag method wherein one chamber contains lipid, a second chamber contains a sterile carbohydrate solution, and a third chamber contains a sterile amino acid solution, and a separate container comprises soluble FePPi. The soluble FePPi may be a sterile solution, or in another embodiment, is in a solid form that can be aseptically solubilized with a pharmaceutically acceptable excipient prior to addition to the parenteral nutrition composition. Similarly, a four-chamber bag is contemplated, where one chamber contains a sterile solution of soluble FePPi, a second chamber contains a sterile carbohydrate solution, a third chamber contains a sterile amino acid solution and a fourth chamber contains lipid. Other components may be added subsequent to admixing or may be added to a solution, for instance, to the carbohydrate solution, prior to admixing.

The invention further provides kits for practice of the present invention. In one embodiment, a kit is provided comprising a first container containing a first composition comprising amino acids, carbohydrates and a pharmaceutically acceptable carrier, and a second container containing a second composition comprising lipid. At least one of the first and second compositions contains soluble FePPi, or soluble FePPi is contained in a separate container for addition to either the first or second containers. The combined amount of soluble FePPi in the first and second containers provides a therapeutically effective amount of iron to the subject, in the form of soluble FePPi. The kit is adapted for separate intravenous infusion of the first and second compositions, when soluble FePPi is contained in at least one of them. Instructions for use, for providing parenteral nutrition to a subject, are optionally provided in the kit.

In another embodiment of the invention, a kit comprises a single container comprising soluble ferric pyrophosphate, amino acids, carbohydrate, lipid, a pharmaceutically acceptable carrier, and optional instructions for use for providing parenteral nutrition to a subject though administration of the composition In another embodiment, a kit comprises at least soluble FePPi in a first container and lipid in a second container. The kit also comprises instructional material regarding the preparation of a parenteral nutrition composition comprising soluble FePPi and lipid present in the kit and exogenously provided amino acids and carbohydrate. This embodiment of the kit is therefore useful with dual-chamber bags, wherein one chamber comprises a sterile amino acid solution and the second chamber contains a sterile carbohydrate solution. Such dual-chamber bags are commercially available. In another embodiment, the kit further comprises one or more of a sterile solution of amino acids and a sterile carbohydrate solution. In an embodiment, a kit comprises separate sterile containers of soluble FePPi, lipid, amino acids and carbohydrate, and instructional material describing the preparation of a parenteral nutrition composition using the components provided in the kit The soluble FePPi in the kits of the invention may be present in the kit as a sterile solution in a pharmaceutically acceptable excipient or in solid form that can be aseptically solubilized with a pharmaceutically acceptable excipient prior to admixing to prepare a parenteral nutrition composition of the invention. A container of a pharmaceutically acceptable excipient is optionally provided in the kit with soluble FePPi in solid form. Lipid in a kit of the invention is preferably in the form of a lipid emulsion. The carbohydrate in a kit of the invention is preferably dextrose.

Physico-Chemical Stability

The composition of the invention is physico-chemically stable for at least about 24 hours, preferably at least about 30 hours, following preparation, when maintained at about 25° C. Physico-chemical stability may be assessed, for example, by assessing the globule size distribution and emulsion integrity of the composition, including examining the composition for cracking and creaming of the lipid component. and phase-separation (Driscoll et al., 1995, *Am. J. Health-Syst. Pharm.* 52:623-634; Vaughan et al., 1990, *Am. J. Hosp. Pharm.* 47:1745-1748).

Two criteria have been proposed by the U.S. Pharmacopeiea ("USP") to verify the stability of lipid emulsions ("Globule Size Distribution in Lipid Injectable Emulsions" (Chapter <729>), Proposed chapter, In-process revision, Pharm. Forum 31:1448-1453). The first criterion is the intensity-weighted mean droplet size (MDS), which is expressed in nanometers (nm) and is measured using dynamic light scattering. MDS is an important qualitative measure of the extent of homogenization of a lipid emulsion. The second measure, the large-diameter tail of the globule size distribution (GSD), is expressed as the volume-weighted percent of fat greater than 5 μm ("PFAT5") and is determined using light extinction employing a single-particle optical sensing technique. Globule size data are normalized to report the percentage of fat in the test articles that is present as particles of greater than 5 μm in diameter. A 5-μm dimension was chosen as the determinant of emulsion stability in testing the compositions of the invention. Five-μm represents the minimum size capable of obstructing the smallest pulmonary capillaries, which have an internal diameter of 4-9 μm, and causing an embolic syndrome.

For lipid injectable emulsions suitable for pharmaceutical applications, the upper USP limit for MDS is 500 nm and for PFAT5 is 0.05%. The PFAT5 criterion is a reproducible measure of the extreme globule outlier population of the globule size distribution and reflects changes in the large-diameter tail long before changes in the MDS are measurable. Furthermore, the population of these large-diameter fat globules (i.e., greater than 5 μm) in stable lipid emulsions has been reported to be uniformly less than 0.05%, and when the PFAT5 population increases to 0.4%, visual evidence of instability (i.e., phase separation) is often detected. Accordingly, the PFAT5 criterion provides a quantitative measurement of globule size distribution and is the stability-indicating measurement indicated in <729> for lipid injectable emulsions.

The compositions of the invention are characterized by an intensity-weighted MDS of less than about 500 nm, preferably less than about 300 nm, when the composition is maintained at a temperature of about 25° C. The compositions of the invention are also characterized by a large-diameter tail of the GSD, expressed as the PFAT5, of less than about 0.05%, preferably less than about 0.03%, when the composition is maintained at a temperature of about 25° C.

Method of Using the Composition

The compositions of the invention may be administered to provide parenteral nutrition comprising bioavailable iron to an individual. In an embodiment of the invention, the individual requires bioavailable iron to maintain an acceptable nutritional status. In another embodiment, the individual requires bioavailable iron to treat an iron deficiency disorder.

The compositions of the invention may be administered to animals, particularly a warm-blooded animal. Preferably, the individual is a primate. More preferably, the individual is a human.

Candidates for parenteral nutrition comprising bioavailable iron include, for example, patients suffering from Crohn's disease, ischemic bowel disease, gastrointestinal motility disorders, congenital bowel defect, hyperemesis gravidarum, chronic pancreatitis, radiation enteritis, chronic adhesive obstructions, cystic fibrosis, cancer, and AIDS. Patients with critical illnesses such as burns, abdominal trauma or surgery, and sepsis also are also candidates for parenteral nutrition therapy comprising bioavailable iron.

The iron-containing parenteral nutrition compositions of the present invention are administered parenterally, principally intravenously. Generally, details of administration, such as rate of administration, total volume to be administered, frequency of administration and duration of administration, are determined by considerations that are conventional for parenteral nutritional compositions and treatment of iron deficiency and are known to the skilled artisan.

The components of the parenteral nutrition compositions of the invention may be administered in admixture as a single composition. It is also contemplated that the components may be administered separately, in separate infusions, although this may be less convenient.

According to one embodiment of separate infusions, the method of parenteral nutrition comprises administering a first composition comprising amino acids, carbohydrates and a pharmaceutically acceptable carrier, and administering a second composition comprising lipid. At least one of the first and second compositions contains a therapeutically effective amount of soluble FePPi. The separate compositions may be provided in kit form, as described above.

The particular dose for each specific patient depends on diverse factors, including, for example, the age, the body weight, the general state of health, the sex, and the diet of the patient; on the time and route of administration; on the rate of iron loss; on the combination of medications being taken by the patient; and on the severity of the particular disorder for which therapy is being given, e.g., the hemoglobin level of the patient, level of serum transferrin saturation, ferritin concentration, etc. The skilled artisan is familiar with the guidelines for the amount, frequency and duration of iron therapy for maintaining nutrition or for treating an iron deficiency disorder. In general, anemic patients will receive a higher dose of iron, which may be administered more frequently and for a longer treatment duration. Suitable dosages by any method of administration may be conventionally determined in accordance with routine experiments, clinical tests and/or conventional procedures in consideration of the iron levels desired to be achieved, e.g., in preventing or treating iron deficiency or iron deficiency anemia. Generally, daily iron dosage of about 1-1000 mg is suitable. This dosage range is intended to be non-limiting since, in all cases, higher or lower amounts may be administered when appropriate.

While not wishing to be bound by any particular rationale or theory, it is believed that the iron-containing compositions of the present invention exhibit iron bioavailability and absence of toxicities, following their intravenous administration to a subject, because they deliver iron directly to circulating transferrin in a physiological manner that prevents an increase in the concentration of free iron in the systemic circulation. This is in contrast to conventional colloidal iron compounds, which, after intravenous administration, have to be processed in the reticuloendothelial system of the recipient before iron is delivered to transferrin. Patients with inflammatory states, such as kidney failure, HIV, inflammatory bowel disease, cancer or chronic infections, often have reticuloendothelial block and do not efficiently release iron from reticuloendothelial stores. Therefore, administration of iron in a parenteral nutrition composition as disclosed in the present invention is believed to benefit such patients by directly promoting binding of iron to transferrin, thereby overcoming the reticuloendothelial block.

It is believed that the soluble FePPi-containing parenteral nutrition compositions of the present invention do not cause or contribute to hypocalcemia. Another metal pyrophosphate complex, stannous pyrophosphate, has been reported to cause hypocalcemia and immediate toxic effects. Since ferric ion forms a stronger complex to pyrophosphate than does stannous ion or calcium ion, hypocalcemia is not expected to be a side affect of soluble ferric pyrophosphate administration. Indeed, soluble FePPi may inhibit calcification by providing pyrophosphate, a very potent inhibitor of vascular and soft-tissue calcification.

The practice of the invention is illustrated by the following non-limiting example.

EXAMPLES

Example 1

Preparation of a Soluble FePPi Solution Suitable for Admixture with a Parenteral Nutrition Composition A formulation of soluble FePPi in sterile water is prepared in the following manner. Two hundred (200) grams of soluble ferric pyrophosphate (equivalent to ~20 grams of elemental iron) is added to a glass-lined vessel containing 4 liters of purified water that has been sparged with nitrogen USP for thirty minutes to reduce the oxygen content. Nitrogen overpressure is maintained during manufacturing. When dissolution is complete, the green solution is passed through a nylon filter having a 0.22 µm pore-size (a sterilizing filter) and collected in a sterile glass-lined vessel. Amber vials are filled with aliquots of the sterile formulation and are closed with PTFE-lined stoppers and capped with aluminum crimp seals. Vials containing 50 mg/ml soluble ferric pyrophosphate solution (about 5 mg of elemental iron/ml) are thus obtained.

Example 2

Parenteral Nutrition Composition Comprising Soluble FePPi and Lipid

To study the effect of soluble FePPi on nutritional emulsions during storage under typical conditions, the studies of Driscoll et al. (1995), supra, were duplicated, using soluble FePPi rather than colloidal iron dextran.

Forty-five (45) clinically-relevant, intravenous nutritional formulations were prepared (Table 4). The formulations contained the following: (1) amino acids (range, 2.5-7% (w/v)); (2) hydrated glucose (range, 5-20% (w/v)); (3) lipid emulsion (range, 2-5% (w/v)); (4) monovalent cations (sodium and potassium, range, 0-150 mEq/L); (5) divalent cations (calcium and magnesium, range, 4-20 mEq/L) and (6) iron (0-10 mg of elemental iron/L) supplied as soluble FePPi. The ranges of concentrations selected represent amounts frequently used in patients receiving parenteral nutrient therapy.

Each formulation, without soluble FePPi, was aseptically prepared as a 1.5-L preparation in ethylene-vinyl acetate infusion bags under sterile conditions in a Class 100 laminar-airflow hood by using an automated compounder. Formulations were prepared in triplicate. A solution of soluble FePPi in water was prepared by dissolving 100 mg of soluble FePPi in 5 mL of sterile water. An appropriate volume of a solution of soluble FePPi in water was then added manually to the final admixture to obtain the desired concentration of iron as soluble FePPi in the PN test preparation (last column of Table 4). After compounding, the formulations were immediately transferred to the laboratory for analysis at Time 0, and then placed in a temperature-controlled chamber set at 25±2° C. throughout each 30 hour investigation.

TABLE 4

Composition of Parenteral Nutrition Test Preparations

| Formulation No. | Amino Acids (% w/v) | Dextrose (% w/v) | Fat (% w/v) | Monovalent Cations (mEq/l) | Divalent Cations (mEq/l) | Iron (mg/l) |
|---|---|---|---|---|---|---|
| 1 | 7 | 12.5 | 3.5 | 75 | 12 | 5 |
| 2 | 4.75 | 5 | 3.5 | 75 | 12 | 5 |
| 3 | 3.4 | 17 | 4.4 | 30 | 7.2 | 2 |
| 4 | 3.4 | 17 | 2.6 | 30 | 16.8 | 2 |
| 5 | 6.1 | 17 | 2.6 | 105 | 7.2 | 8 |
| 6 | 3.4 | 17 | 4.4 | 105 | 16.8 | 2 |
| 7 | 4.75 | 12.5 | 3.5 | 75 | 12 | 0 |
| 8 | 3.4 | 17 | 2.6 | 105 | 16.8 | 8 |
| 9 | 3.4 | 17 | 4.4 | 105 | 7.2 | 8 |
| 10 | 4.75 | 12.5 | 3.5 | 75 | 12 | 10 |
| 11 | 3.4 | 17 | 4.4 | 30 | 16.8 | 8 |
| 12 | 4.75 | 12.5 | 3.5 | 150 | 12 | 5 |
| 13 | 6.1 | 17 | 2.6 | 30 | 16.8 | 8 |
| 14 | 6.1 | 17 | 2.6 | 105 | 16.8 | 2 |
| 15 | 3.4 | 8 | 2.6 | 105 | 16.8 | 2 |
| 16 | 4.75 | 12.5 | 3.5 | 75 | 4 | 5 |
| 17 | 6.1 | 8 | 2.6 | 30 | 16.8 | 2 |
| 18 | 6.1 | 8 | 2.6 | 105 | 7.2 | 2 |
| 19 | 4.75 | 12.5 | 3.5 | 75 | 12 | 5 |
| 20 | 6.1 | 8 | 4.4 | 30 | 7.2 | 2 |
| 21 | 3.4 | 17 | 2.6 | 30 | 7.2 | 8 |
| 22 | 3.4 | 8 | 4.4 | 105 | 16.8 | 8 |
| 23 | 2.5 | 12.5 | 3.5 | 75 | 12 | 5 |
| 24 | 6.1 | 8 | 2.6 | 30 | 7.2 | 8 |
| 25 | 3.4 | 8 | 4.4 | 30 | 16.8 | 2 |
| 26 | 6.1 | 8 | 4.4 | 105 | 16.8 | 2 |
| 27 | 6.1 | 17 | 2.6 | 30 | 7.2 | 2 |
| 28 | 6.1 | 8 | 4.4 | 105 | 7.2 | 8 |
| 29 | 6.1 | 8 | 4.4 | 30 | 16.8 | 8 |
| 30 | 4.75 | 12.5 | 2 | 75 | 12 | 5 |
| 31 | 4.75 | 12.5 | 3.5 | 0 | 12 | 5 |
| 32 | 6.1 | 17 | 4.4 | 30 | 16.8 | 2 |
| 33 | 6.1 | 17 | 4.4 | 105 | 16.8 | 8 |
| 34 | 3.4 | 17 | 2.6 | 105 | 7.2 | 2 |
| 35 | 3.4 | 8 | 4.4 | 30 | 7.2 | 8 |
| 36 | 3.4 | 8 | 2.6 | 30 | 16.8 | 8 |
| 37 | 6.1 | 17 | 4.4 | 30 | 7.2 | 8 |
| 38 | 3.4 | 8 | 2.6 | 30 | 7.2 | 2 |
| 39 | 3.4 | 8 | 2.6 | 105 | 7.2 | 8 |
| 40 | 4.75 | 20 | 3.5 | 75 | 12 | 5 |
| 41 | 4.75 | 12.5 | 3.5 | 75 | 20 | 5 |
| 42 | 4.75 | 12.5 | 5 | 75 | 12 | 5 |
| 43 | 6.1 | 8 | 2.6 | 30 | 16.8 | 8 |
| 44 | 3.4 | 8 | 4.4 | 105 | 7.2 | 2 |
| 45 | 6.1 | 17 | 4.4 | 105 | 7.2 | 2 |

Physical assessments of the formulations included dynamic light scattering (DLS) for the submicron population of droplets for MDS of the dispersed lipid phase, and pH at the outset and end of study. Large fat globules (5 μm), indicative of the stability of the admixture, were measured using a light obscuration or extinction method, employing a single-particle optical sensing technique (LE/SPOS). The large-diameter data were expressed as the volume-weighted percentage of fat greater than five micrometers diameter (PFAT5). These measurements were performed at time 0 (immediately after preparation of the formulations), and then at Time 6, 24 and 30 hours storage at 25° C.±2° C.

Continuous variables were expressed as mean±S.D. and tested by appropriate parametric analyses. Dichotomous variables were compared by chi-square analysis. The light obscuration data were analyzed by multiple stepwise regression analysis. To assist in identifying and grouping stable versus unstable test emulsions, sensitivity and specificity analyses and chi-square analysis were performed to rule out the lot number or source of intravenous fat emulsion as a factor influencing emulsion stability. The percentage of fat particles of greater than 5 μm in diameter present at each interval was the dependent variable affected by the six factors that are independent variables. Data obtained from dynamic light scatter and physical assessments were analyzed by either unpaired t tests of independent groups when emulsions are separable into stable vs. unstable groups. Chi-square analysis was also used to assess the influence of the expression based on the Schultze-Hardy rule, termed the critical aggregation number, in predicting stability. The a priori level of significance was 0.05. Commercial statistical analysis software was used for statistical analysis.

The results are summarized in Table 5.

TABLE 5

Stability of Parenteral Nutrition Admixtures Containing Soluble FePPi

| Formulation No. (Note 1) | Population of fat globules exceeding 5 μm (PFAT5) (%) Time (Hr) | | | | Mean droplet size (MDS) (nm) Time (Hr) | |
|---|---|---|---|---|---|---|
| | 0 | 6 | 24 | 30 | 0 | 30 |
| 1 | 0.007 | 0.017 | 0.008 | 0.014 | 273 | 274 |
| 2 | 0.018 | 0.017 | 0.007 | 0.006 | 277 | 276 |

TABLE 5-continued

Stability of Parenteral Nutrition Admixtures Containing Soluble FePPi

| Formulation No. (Note 1) | Population of fat globules exceeding 5 µm (PFAT5) (%) Time (Hr) | | | | Mean droplet size (MDS) (nm) Time (Hr) | |
|---|---|---|---|---|---|---|
| | 0 | 6 | 24 | 30 | 0 | 30 |
| 3 | 0.007 | 0.011 | 0.009 | 0.047 | 274 | 276 |
| 4 | 0.013 | 0.011 | 0.007 | 0.005 | 279 | 276 |
| 5 | 0.022 | 0.018 | 0.010 | 0.009 | 276 | 276 |
| 6 | 0.028 | 0.021 | 0.006 | 0.004 | 276 | 277 |
| 7 | 0.010 | 0.007 | 0.003 | 0.003 | 283 | 284 |
| 8 | 0.017 | 0.013 | 0.007 | 0.009 | 289 | 253 |
| 9 | 0.027 | 0.022 | 0.008 | 0.008 | 285 | 281 |
| 10 | 0.010 | 0.006 | 0.003 | 0.002 | 273 | 278 |
| 11 | 0.014 | 0.012 | 0.006 | 0.006 | 285 | 279 |
| 12 | 0.040 | 0.027 | 0.009 | 0.009 | 284 | 281 |
| 13 | 0.004 | 0.004 | 0.004 | 0.004 | 274 | 274 |
| 14 | 0.026 | 0.023 | 0.010 | 0.007 | 282 | 283 |
| 15 | 0.011 | 0.008 | 0.005 | 0.004 | 283 | 279 |
| 16 | 0.016 | 0.013 | 0.007 | 0.006 | 282 | 286 |
| 17 | 0.017 | 0.019 | 0.003 | 0.006 | 188 | 285 |
| 18 | 0.007 | 0.008 | 0.004 | 0.004 | 284 | 192 |
| 19 | 0.013 | 0.010 | 0.004 | 0.003 | 285 | 189 |
| 20 | 0.010 | 0.009 | 0.006 | 0.005 | 289 | 194 |
| 21 | 0.031 | 0.020 | 0.008 | 0.007 | 285 | 190 |
| 22 | 0.011 | 0.013 | 0.005 | 0.022 | 274 | 182 |
| 23 | 0.015 | 0.011 | 0.015 | 0.030 | 275 | 182 |
| 24 | 0.005 | 0.011 | 0.002 | 0.004 | 275 | 183 |
| 25 | 0.015 | 0.010 | 0.004 | 0.004 | 287 | 159 |
| 26 | 0.045 | 0.029 | 0.013 | 0.009 | 285 | 190 |
| 27 | 0.080 | 0.123 | 0.008 | 0.008 | 289 | 192 |
| 28 | 0.050 | 0.041 | 0.017 | 0.010 | 282 | 188 |
| 29 | 0.007 | 0.017 | 0.006 | 0.017 | 273 | 183 |
| 30 | 0.006 | 0.004 | 0.004 | 0.014 | 269 | 181 |
| 31 | 0.003 | 0.004 | 0.004 | 0.017 | 278 | 223 |
| 32 | 0.006 | 0.009 | 0.010 | 0.009 | 278 | 185 |
| 33 | 0.039 | 0.028 | 0.019 | 0.010 | 281 | 187 |
| 34 | 0.011 | 0.016 | 0.006 | 0.018 | 277 | 182 |
| 35 | 0.008 | 0.011 | 0.005 | 0.019 | 278 | 185 |
| 36 | 0.008 | 0.011 | 0.010 | 0.020 | 271 | 182 |
| 37 | 0.006 | 0.020 | 0.010 | 0.012 | 278 | 187 |
| 38 | 0.017 | 0.013 | 0.014 | 0.009 | 279 | 186 |
| 39 | 0.018 | 0.013 | 0.005 | 0.009 | 274 | 181 |
| 40 | 0.063 | 0.040 | 0.085 | 0.013 | 281 | 188 |
| 41 | 0.024 | 0.037 | 0.010 | 0.017 | 273 | 180 |
| 42 | 0.008 | 0.007 | 0.011 | 0.014 | 280 | 185 |
| 43 | 0.082 | 0.033 | 0.013 | 0.027 | 285 | 188 |
| 44 | 0.008 | 0.012 | 0.009 | 0.020 | 277 | 185 |
| 45 | 0.081 | 0.042 | 0.009 | 0.008 | 285 | 193 |

(Note 1):
The composition of each formulation is provided in Table 4.

A balanced fractional factorial design was used to study the influence of six independent factors on the stability of 45 clinically-relevant, intravenous nutritional formulations during storage under typical conditions. The data indicate that soluble FePPi did not significantly alter the stability of nutritional emulsions or disrupt their integrity. No increases in mean droplet sizes (MDS) were observed. No increases in the percentage of fat particles >5 µM in diameter (PFAT5) were observed. Unexpectedly, during the 30-hour period of testing, no unstable emulsions were observed. Notably, there were no disruptions of emulsion integrity, such as creaming, phase-separation, or visible fat globule formation.

This experiment thus demonstrates that formulations that are compounded aseptically from soluble FePPi and parenteral nutrient compositions are stable. This result is in stark contrast to what is observed with parenteral nutrition compositions containing conventional colloidal iron compounds (Driscoll et al., 1995, supra).

Example 3

Clinical Administration of Parenteral Nutrition Composition with Soluble FePPi to Anemic Subjects A patient with a history of bowel resection, secondary to inflammatory bowel disease is currently receiving TPN therapy at home. The patient develops iron deficiency anemia, secondary to ongoing bloody diarrhea and malabsorption of iron. The patient is unable to take iron supplements by mouth due to bloating and diarrhea. Erythropoietin therapy is not effective, since the patient has iron deficiency.

Aseptic addition of 15 mg soluble FePPi to a conventional parenteral nutrition composition provides an iron-replete parenteral nutrition admixture that is administered to the patient intravenously over 6 hours every day. Treatment in this manner effectively corrects iron deficiency anemia over a period of 3 months. Subsequently, the dose of soluble FePPi is reduced to 20 mg per liter of parenteral nutrition composition administered 3 times per week.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

I claim:

1. A composition suitable for parenteral nutrition comprising:
a therapeutically effective amount of soluble ferric pyrophosphate; lipid; amino acids; carbohydrate and a pharmaceutically acceptable carrier.

2. The composition according to claim 1, wherein the composition is physic-chemically stable for at least about 24 hours following preparation, when the composition is maintained at about 25° C.

3. The composition according to claim 1, herein the mean droplet size of the composition is less than about 500 nanometers for at least about 30 hours following preparation, when the composition is maintained at about 25° C.

4. The composition according to claim 1, wherein the globule size distribution of the composition, expressed as the volume-weighted percent of fat greater than 5 µm in the composition, is less than about 0.05% at about 30 hours following preparation, when the composition is maintained at about 25° C.

5. The composition according to claim 1, wherein elemental iron as soluble ferric pyrophosphate is present in the range of about 1 mg/L to about 150 mg/L.

6. The composition according to claim 5, wherein elemental iron as soluble ferric pyrophosphate is present in the range of about 1 mg/L to about 50 mg/L.

7. The composition according to claim 1, wherein the amino acids are present in the range from about 2.5% to about 7% (w/v).

8. The composition according to claim 1, wherein the lipid is present in the range from about 2% to about 5% (w/v).

9. The composition according to claim 1, wherein the carbohydrate is present in the range from about 5% to about 20% (w/v).

10. The composition according to claim 1, wherein the carbohydrate comprises dextrose.

11. The composition according to claim 1, further comprising one or more additional components selected from the group consisting of electrolytes, medicaments, vitamins and trace minerals not containing iron.

12. A method for preparing a composition suitable for parenteral nutrition, the method comprising aseptically combining soluble ferric pyrophosphate, lipids, amino acids, carbohydrate and a pharmaceutically acceptable carrier.

13. The method of claim 12, comprising first forming a composition comprising amino acids, carbohydrate and a pharmaceutically acceptable carrier and mixing therewith soluble ferric pyrophosphate and lipid.

14. The method of claim 12, comprising combining soluble ferric pyrophosphate with a composition comprising lipid, amino acids, carbohydrate and a pharmaceutically acceptable carrier.

15. The method according to claim 12, wherein elemental iron, as the soluble ferric pyrophosphate, is present in the composition in the range from about 1 mg/L to about 150 mg/L.

16. The method according to claim 15, wherein elemental iron, as the soluble ferric pyrophosphate, is present in the composition in the range from about 1 mg/L to about 50 mg/L.

17. The method according to claim 15, wherein the composition is physico-chemically stable for at least about 4 hours following preparation, when the composition is maintained at about 25° C.

18. The method according to claim 12, wherein the mean droplet size of the composition is less than about 500 nanometers for at least about 30 hours following preparation, when the composition is maintained at about 25° C.

19. The method according to claim 12, wherein the globule size distribution of the composition, expressed as the volume-weighted percent of fat greater than 5 μm in the composition, is less than about 0.05% at about 30 hours following preparation, when the composition is maintained at about 25° C.

20. The method according to claim 12, wherein said carbohydrate comprises dextrose.

21. A method for providing parenteral nutrition comprising bioavailable iron to an individual, the method comprising administering a composition according to claim 1.

22. The method according to claim 21, wherein elemental iron, as soluble ferric pyrophosphate, is present in the administered composition in the range from about 1 mg/l to about 150 mg/l.

23. The method according to claim 21, wherein the composition is physic-chemically stable for at least about 24 hours following preparation, when the composition is maintained about 25° C.

24. The method according to claim 21, wherein the mean droplet size of the composition is less than about 500 nanometers for at least about 30 hours following preparation, when the composition is maintained at about 25° C.

25. The method according to claim 21, wherein the globule size distribution of the composition, expressed as the volume-weighted percent of fat greater than 5 μm in the composition, is less than about 0.05% at about 30 hours following preparation, when the composition is maintained at about 25° C.

26. A method for providing parenteral nutrition, comprising bioavailable iron to an individual, the method comprising intravenously administering a first composition comprising amino acids, lipid carbohydrates and a pharmaceutically acceptable carrier, and intravenously administering a second composition comprising lipid, at least one of the first and second compositions containing soluble ferric pyrophosphate.

27. A kit for providing parenteral nutrition comprising a first container containing a first composition comprising amino acids, lipid, carbohydrates and a pharmaceutically acceptable carrier, a second container containing a second composition comprising lipid, wherein at least one of the first and second compositions contains soluble ferric pyrophosphate.

* * * * *

UNITED STATES PATENT AND TRADEMARK OFFICE
CERTIFICATE OF CORRECTION

PATENT NO. : 9,161,951 B2
APPLICATION NO. : 11/644527
DATED : October 20, 2015
INVENTOR(S) : Ajay Gupta Page 1 of 1

It is certified that error appears in the above-identified patent and that said Letters Patent is hereby corrected as shown below:

In the Claims:

At Column 20, line 37, "physic-chemically" should be -- physico-chemically --.

At Column 20, line 40, "herein the" should be -- wherein the --.

At Column 22, line 9, "physic-chemically" should be -- physico-chemically --.

At Column 22, lines 10-11, "maintained about" should be -- maintained at about --.

At Column 22, line 25, "lipid" should be -- lipid, --.

Signed and Sealed this
Twenty-ninth Day of March, 2016

Michelle K. Lee
*Director of the United States Patent and Trademark Office*